(12) United States Patent
Mäenpää et al.

(10) Patent No.: US 7,799,171 B2
(45) Date of Patent: Sep. 21, 2010

(54) REELING METHOD AND SYSTEM AS WELL AS AN MEASURING APPARATUS

(75) Inventors: Tapio Mäenpää, Helsinki (FI); Jari Tiitta, Kellokoski (FI); Petteri Lannes, Jokela (FI); Rami Vanninen, Kellokoski (FI); Tatu Pitkänen, Järvenpää (FI); Heikki Kettunen, Espoo (FI); Matti Innala, Järvenpää (FI); John Shakespeare, Kuopio (FI); Toni Heikkilä, Kotka (FI); Topi Tynkkynen, Vantaa (FI); Teppo Kojo, Mäntsälä (FI); Risto Mäkinen, Mäntsälä (FI); Marko Tiilikainen, Kellokoski (FI); Matti M. Kemppainen, Jokela (FI)

(73) Assignee: Metso Paper, Inc., Helsinki (FI)

( * ) Notice: Subject to any disclaimer, the term of this patent is extended or adjusted under 35 U.S.C. 154(b) by 801 days.

(21) Appl. No.: 11/571,207

(22) PCT Filed: Jul. 1, 2005

(86) PCT No.: PCT/FI2005/050265
§ 371 (c)(1),
(2), (4) Date: May 11, 2007

(87) PCT Pub. No.: WO2006/003262
PCT Pub. Date: Dec. 1, 2006

(65) Prior Publication Data
US 2008/0017341 A1 Jan. 24, 2008

(30) Foreign Application Priority Data
Jul. 1, 2004 (FI) .................................. 20040919
Jun. 27, 2005 (FI) .................................. 20055348

(51) Int. Cl.
*D21F 11/00* (2006.01)
(52) U.S. Cl. ..................................... 162/198
(58) Field of Classification Search ................. 162/198, 162/263; 73/862.55, 159
See application file for complete search history.

(56) References Cited
U.S. PATENT DOCUMENTS

| 5,048,353 | A | * | 9/1991 | Justus et al. ............. 73/862.55 |
| 5,052,233 | A | | 10/1991 | Rantala |
| 5,535,627 | A | | 7/1996 | Swanson et al. |
| 5,649,448 | A | | 7/1997 | Koskimies et al. |
| 6,845,281 | B1 | | 1/2005 | Griech |
| 2002/0043108 | A1 | | 4/2002 | Schafer et al. |
| 2003/0230140 | A1 | | 12/2003 | Eccardt et al. |

FOREIGN PATENT DOCUMENTS

| CA | 2222839 A1 | 5/1998 |
| DE | 1077192 | 3/1960 |
| EP | 0517830 B1 | 1/1994 |
| EP | 0588776 A2 | 3/1994 |
| EP | 1541762 A1 | 6/2005 |
| EP | 1541762 B1 | 6/2005 |
| FI | 80522 | 2/1990 |
| GB | 758538 | 10/1956 |
| GB | 1328158 | 8/1973 |
| SE | 521580 C2 | 11/2003 |
| WO | 97/24595 A1 | 7/1997 |
| WO | 99/00547 A1 | 1/1999 |
| WO | 03/076320 A1 | 9/2003 |
| WO | 2006/003262 A1 | 1/2006 |

OTHER PUBLICATIONS

EP 1541762, Date Published Jun. 2005, machine translation.*
International Preliminary Report on Patentability issued in PCT/FI2005/050265.
International Search Report issued in PCT/FI2005/050265.
Translation of Abstract in EP 1541762.
Translation of Abstract in WO 9900547.
Translation of Abstract of SE 521580.
International Preliminary Report on Patentability issued in PCT/FI2005/050265, Oct. 2005.
International Search Report issued in PCT/FI2005/050265, Aug. 2006.
Translation of Abstract in EP 1541762, Jun. 2005.
Translation of Abstract in WO 9900547, Jul. 1999.
Translation of Abstract of SE 521580, Nov. 2003.

* cited by examiner

Primary Examiner—Mark Halpern
(74) Attorney, Agent, or Firm—Stiennon & Stiennon

(57) ABSTRACT

A method and a system to control a reeling profile of a material web reel (30), when, in the forming of a material web reel (30), a web is reeled around a reeling core and when in an adjustment of CD-directional profiles of the web reel, profiling devices (8) have been applied. For adjusting quality profiles and reeling profiles of the web, profiling devices are managed with the help of profile measurings of the roller nip and/or of the profile measurings of the reel (30), which are obtained from the reel-up (2). A measuring device (40) for a measuring of a CD-directional hardness profile of the fiber web reel includes a measuring head (43), which is connected with a loading means (41, 42), which loads the measuring head against the fiber web reel. The motion course of the measuring head is linear.

16 Claims, 3 Drawing Sheets

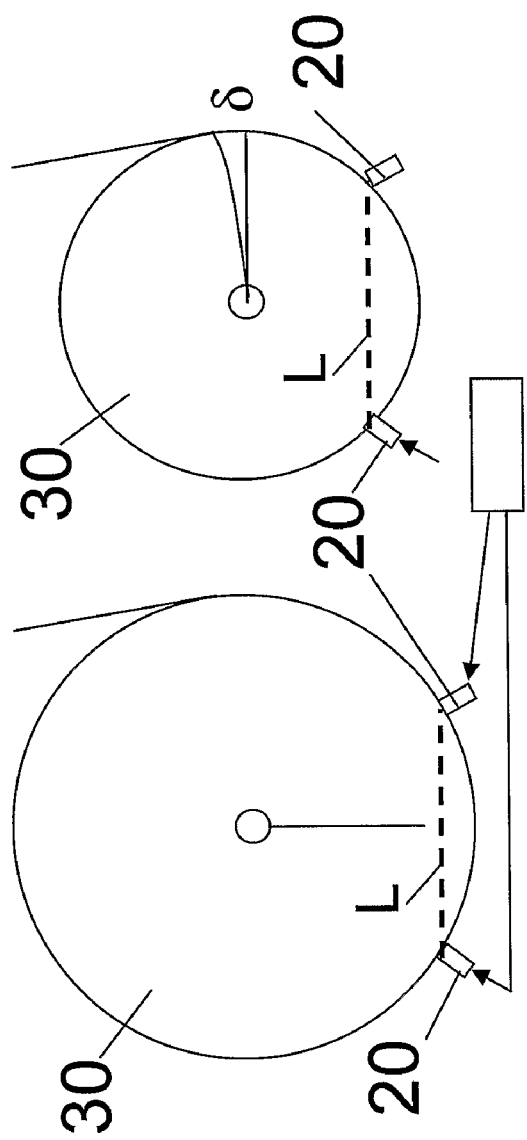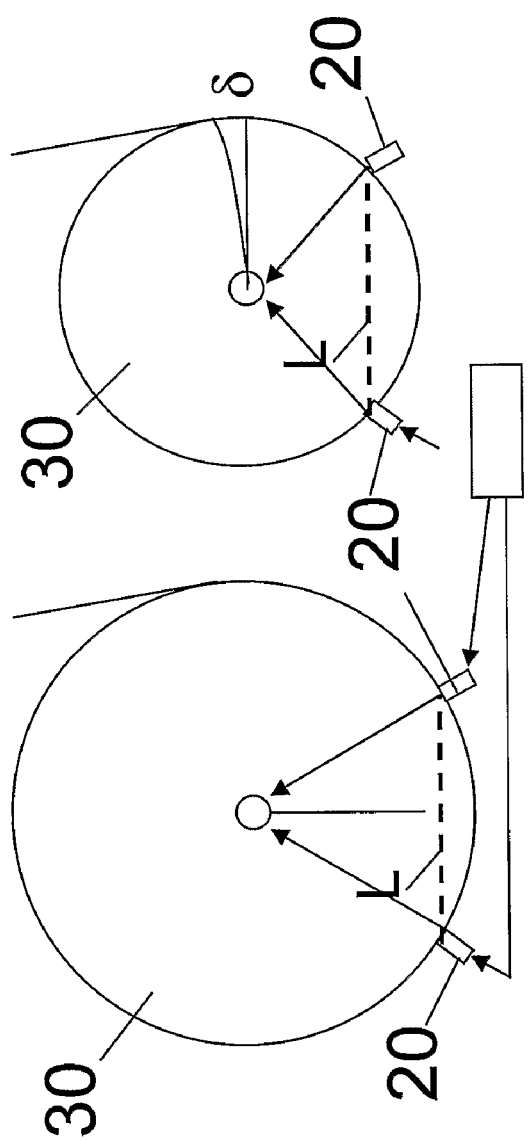

US 7,799,171 B2

REELING METHOD AND SYSTEM AS WELL AS AN MEASURING APPARATUS

CROSS REFERENCES TO RELATED APPLICATIONS

This application is a U.S. national stage application of International App. No. PCT/FI2005/050265, filed Jul. 1, 2005, the disclosure of which is incorporated by reference herein, and claims priority on Finnish App. No. 20040919, filed Jul. 1, 2004, and Finnish App. No. 20055348, filed Jun. 27, 2005, the disclosures of which are incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The invention in question is connected with the forming of a machine reel or customer reel in the material web machine. The invention out in more detail is connected to the reeling method and to a system as for control a reeling profile a material web reel, like a machine reel or a customer reel.

In the future the processing machines of different material webs are pointed to, for the sake of simplicity, with the qualifier the material web machine, which can be the processing machine of the stretching, web in ever what web-like form. The processing machine of the web is a fiber web machine or a paper machine and/or cardboard machine advantageously. The different webs are referred to with the qualifier in the future for the sake of simplicity, the material web, which is a material web, which stretches advantageously and in general means all kinds of webs; more advantageously, generally a fiber web which means different paper webs and cardboard webs and tissue webs and cloth webs etc.; and especially paper web and/or cardboard web.

A method for commanding the reeling profile of the material web reel has been improved especially as the target of the invention a stretching material web when, in the forming of the reel it is reeled when, profiling devices that have been arranged in the material web machine are used around the reeling core or around a similar heart in regard to CD-the directional, in other words, that is, in regard to a machine direction, MD-direction, a direction in the adjustment of transverse directional profiles and a material web track. A system has also been improved as the target of the invention especially out a stretching material web to command the reeling profile of the material web reel, in the forming of the reel as it is reeled, around the reeling core or around the similar heart, when in the adjustment of the CD-directional profiles of the material web track, profiling devices, which have been arranged in the material web machine, are used. The target of the invention in question also is a measuring device as a special target for the measuring of the CD-directional hardness profile of the material web reel which measuring device includes the measuring end of the hardness indicator, which is connected with the load tool which loads the measuring head against around the one turning when turning and outer surface of its central axis of rotation of the material web reel which grows in the direction of the radius.

In the material web machine, the material web in other words web track is reeled around a reel-up core, a reel-up heart, a center cartridge, a tampur roll, a reel-up iron bar or a similar center element. In the future the center elements of this kind are pointed to for the sake of simplicity with the definition a reeling core. The reel, which is formed in the reeling, is pressed around the reeling core against the reeling cylinder, reeling reel-up or a corresponding, where it is referred to in the future for the sake of simplicity with the definition a reeling reel-up.

In the forming of the reel it is reeled around the reeling core a stretching web. Every additional layer causes the increase in the parallel with the radius strain and the compaction of the layers below. When a layer ends up in inner parts, their circumference will become smaller. A certain circumference is corresponded by a certain stretch, in other words when a stretch becomes smaller, the strain of the web will also become smaller. An equilibrium, where the parallel with the radius of the reel bearing stress and the parallel with the tangent tensile stress reach the regular value if the strain of the web which has dominated in the reeling has been a constant will be reached this way in the inner parts of the reel. A reel becomes tighter and a constant strain state is reached on the deeper from the surface of the reel the smaller it is a ratio between the machine or MD-directional modulus of elasticity and the reel radius directional modulus. Thus by the control of the modulus of elasticity the forming of the homogenous reel can be influenced significantly. In the inner parts of the reel, the MD-directional strain of the web can be even negative. From the point of view of the runnability, even a negative strain is an advantage, because the material web, such as for example paper, does not lose its stretching ability. If a strain is not even and the reel has been forced to be under a varying load, the folding of layers can be perceived especially in the ends in the area of the negative strain. On the surface of the reel, the material web has to be again a subordinate to the tensile stress whereby the stretching ability of surface layers becomes smaller.

This explains in its part during the next unwinding, in the so-called flying seaming, the track breaks, which take place more generally than would be normal.

The even properties of the web in the CD-direction also are important to accomplish the good quality of the reel. However, there are always CD-directional variations in practice in the web. The thickness of the material web and the density should be even in the strain, which dominates in the reel so that the homogenous reel from its structure would be possible. Furthermore, the length and stretchability of the web affect the stability of the strains of the reel in addition to thickness and the compressibility. Perhaps in the reel, an even strain is obtained in the direction of the axis if the relation of the length variation and thickness variation of the web is constant ($\pi$). 3 µm local change, for example, in the thickness (65 g/m², 1200 kg/m³: 57 µm 2200 among others/54 µm 2148 mm) 26 mm causes the change in the radius of the reel. The uneven hardness profile of the CD-direction can come to the reel thus when at the same time the thick section of the web is a tight and thin loose section.

Many kinds of faults to be perceived are found in the reels also with eyes. The good reel should be cylinder-shaped and homogenous from its structure. The most ordinary reeling faults are the loose bottom, so-called pot head, bags, rents, the wrinkles and the non-round reels. In the level of the technique the one forming and/or becoming to be the identification of the reel faults of the reel is known many kinds of solutions.

It will form into a problem in material web machines to be equipped with in-line cutting stations, production disturbances that are caused by the quality of the machine reel on cutting stations, operation of which is automated and occupation of which is minor. With the present methods quality of the reel; that is, reel-up faults, a handling of the machine reel, an intermediate storing fault; one cannot control carefully enough when the reel is transferred to the unwinding of the cutting station, in-line. Furthermore, the defects in quality of the machine reel cause track breaks and wreck on the cutting station and on the other hand, because of on the other hand, the decrease of the operating personnel are not labour to the dismantling of a break reject, which is created with the cutting station and of break situations any more.

It is essential that in addition to the reeling tightness (WIN-WOT) caused of a reeling nip and reeling power the smoothness of the CD-directional hardness profile of the forming reel also affects the forming of the reel. The line load of the nip and the circumferential pulling or reeling power, by which the internal tightness δ of the reel mainly forms, affect strongest to the tightness inside the reeling nip. The modern technology can be used to measure only line load, track tightness and torque in the reeling. Because of this, the real tightness of the reel cannot be controlled by the modern technology, in the reeling process; therefore the control and adjustment of the tightness inside the reel are indeed more empirical nowadays.

In addition to an ocular reel examination, it is felt, to examine the reel in the direction of both the shaft of the reel and the radius by measuring different properties from the reel. The parallel with the axis measurings describe the good quality of the transversal profile of the paper. Change of the properties of the reel in the direction of the radius the hardness of the reel is again describing the reeling event.

The biggest problem from an uneven parallel with the shaft of the reel CD-cross section profile is a consequence from the air which gets to the reel and can cause the slide of the reel between the layers and even the falling of the reel. When the CD-profile of the reel is not a straight line, the reeling nip will be close to the direction of the shaft of the reel in the direction of the radius of only the forming reel from the thickest sections. In the sections, where the reel is smaller in the direction of its radius and in that case reeling nip will be open more air than if the roller nip would be evenly shut gets in the reel, whereby the reeling profile is direct. When the CD-profile is uneven, the forming ridges will prevent out in the direction of the radius of the reel to the thicker sections of the reel in the entrance of the air which has got in the reel, whereby the air, which reduces the friction and makes the forming of the even and of the good quality reel more difficult essentially stays.

The simplest measuring method for the measuring of the quality of the forming reel is a roding of the reel on the tree stick. Both the voice frequency which is created this way and the bouncing of the tree stick for the surface of the reel describe the hardness of the reel. The automated application of this kind of a measuring is called often with the name, "Back tender's friend", where the hardness profile of the reel is measured with a measure wheel which scans the surface of the reel. Other known methods are a ball bouncing method, Schmidt's hardness indicator and Rho indicator (Beloit). Some of the known methods also are the Cameron test, the tightness measuring and the J-line test. Older methods are a density measuring, which is made by weighing the reel at regular intervals by means of slabbing. The thickness information and grammage of the web can also be calculatorily used to measure the density. The parallel with the shaft of reels variation can be studied by also measuring the diameter or perimeter measure variations.

The reeling event is typically commanded with the help of the line load of the reeling nip, the future track tightness and center paragraph. These so-called reeling parameters change during the reeling for example so that when making a so-called hard bottom, bigger control parameters which then will be reduced when the reeling will proceed will be used to the parameters at the beginning of the reeling. In the CD-direction of the web track to the profiles of the reel, that is, the CD-profiles of the reel is influenced with the oscillating of the reel. With the procedure it is attempted to the fact that the CD-directional (thickness) variations which appear in the web track would not cumulate in the reel to the same section.

In connection with the level of the technique, one can state that in EP publication number 0517830 B1 has been presented, whereby with the help of the stretch slips and/or pressure sensors, censored, a reeling reel-up measuring data to be obtained for example division data of the strain, which it is that the values of the modulus of elasticity of the web in the direction of the radius and tangent of the reel the help can be used to determine and the support powers of the material web during the bottom forming of the reel. Also for example capacitive, fiber optical EMFi transparency sensors can naturally be used instead of the stretch slips and pressure sensors that have been meant for the measuring of the CD-power profile of the nip.

A generally known custom to reduce the CD-profile mistakes of the reel a little is the oscillating 10-50 mm back and forth. In that case, however, this will lead into the problem that at the same time trim-dissipation are caused to both ends of the reel, in other words an oscillating movement of the reel has to be cut at both heads thereof.

Already it is also known that the profile of temperature tightness and track tightness can be measured from the web track in the CD-direction of the web. This kind of a measuring principle is known for a FI patent publication number 80522 and from U.S. Pat. No. 5,052,233.

Already it is still after knowing that micro wave radar, an ultrasound etc., the laser can be used to measure the width and radius of the forming and/or forming reel and the CD-profile of diameter/the radius. In that case it will be seen with the help of the width measuring of the reel if the inner structure of the reel changes and the inner layers of the reel try to slide in the CD-direction and this way "to gush out." This way one can act when the oscillation of the reel is not needed from the traditions any more. One way of measuring, which relates to laser measuring, is known from the applicant's earlier SE patent number 521580 (PCT/SE03/00363), where it is measured instead of the CD-profile the form of the reeling nip locally in the MD-direction.

Another measuring way, which represents the nearest level of the technique to the invention in question, is known from a publication number EP 845655, where the measuring of the profile of the surface of the reel has been presented. According to the presented solution, the measuring head which measures the distance to the surface of the reel goes in parallel in the axis direction of the reel with it at the end of the regular distance. Then the deviations in the CD-profile of the reel can be found out with the movement of the measuring head.

In order to CD-profile a material web reel actively, there is ready known as such three different principles.

A) from its profile the bottom of the reel is softened to the one which had weakened so that the web layers to be reeled will be saved over them B) "Trim" information is utilized, for the diameter of the machine reel optimization and C) There is applied the principle, which is known from the publication DE 1077192, according to which the bottom of the machine reel is profiled with the help of the wedge of the water cutting shifting device.

There is previously known a follow-up device of the CD-directional hardness profile of the reel, which is developed by Metso Paper, Inc. and which is suitable for so-called pope reel-ups, where the changes of machine reels are relatively little. This follow-up device will include the measuring head arranged in the free end of the lever-like turning load tool, which is, when the diameter of the reel increases, against the surface of the reel. However, the weakness of this follow-up device is that the follow-up device is not suitable for reel-ups, where the diameter of the reel will increase remarkably, because the measuring geometry of the follow-up device changes and causes the mistake, which causes considerable investment problems and because the follow-up device requires considerably much space.

Indeed, generally can be stated that the level of the technique describes methods and systems which can be used to follow the CD-profiles of a reel or web.

SUMMARY OF THE INVENTION

A goal of the invention in question is to eliminate or to reduce drawbacks and weaknesses which are related to the known technique at least essentially. According to a general aspect of the invention, the goal is to accomplish a new method for commanding the reeling event of the material web. According to a performance example of the invention in question the goal is to try to command the reeling event and reeling profiles so that, before the calender after the calender and/or the reel-up could be used to control quantities which affect reeling optionally with the calender on the basis of the measurings which are done from a reeling nip, a web track and/or reel. According to another performance example of the invention, the goal is furthermore to make possible, in addition to the reel measurings, the use of information, which has been calculated from a reeling model/-models.

These goals have generally been reached with a method to control a reeling profile of a material web reel, when, in the forming of the reel a stretching material web is reeled around a reeling core or around a similar heart and when in an adjustment of CD-directional profiles of the material web track, profiling devices, which have been arranged in the material web machine, have been applied, for example so that for adjusting quality profiles and reeling profiles of the web profiling devices are managed with the help of profile measurings of the reeling nip and/or of the profile measurings of the reel, which are obtained from the reel-up.

The goals of the invention have generally also been reached with a system to control a reeling profile of a material web reel, when, in the forming of the reel a stretching material web is reeled around a reeling core or around a similar heart and when in an adjustment of the CD-directional profiles of the material web track, profiling devices, which have been arranged in the material web machine, have been applied, for example so that for adjusting quality profiles and reeling profiles of the web profiling devices are managed with the help of profile measurings of the reeling nip and/or of the profile measurings of the reel, which are obtained from the reel-up.

To control the reeling event profiling devices which are located before the reel-up are directed in the process according to the invention so that the CD-profiles of the reel will be as even as possible. In that case the quality measurings of a reel and/or web track will be utilized. For the quality measurings of the profile are advantageous to use an amount of thickness and/or a number of luster and/or an amount of moisture and/or a grammage and/or density and/or an amount of coating and/or a roughness and/or an air permeability of the material web according to the invention. In addition to these measurings, track strain measuring and/or temperature measurings can also be made according to the invention.

In a material web machine, the profiling devices, which are suitable for carrying out of the invention, are among others: profiling CD-reel-ups; humidifiers; vapor boxes; dryers; and profiling track strain organs. The profiling devices of this kind can be located in an optional part or in optional part of a material web machine or before/after of this kind of the part. A head box, pressing part, a wire part, drying part, covering part, glue pressing part and/or calendar part can be mentioned as examples of the suitable parts of the material web machine, according to an advantageous embodiment of the invention the profiling devices are located before a calendar, in a calendar and/or after a calendar.

According to an embodiment of the invention, that has been considered especially advantageous, to actively manage CD-profile of the material web reel, especially to straighten the CD-profile, a narrow strip is cut from a section of the thick web reel in the MD-direction or directly from the surface of the reel with a reel-up. According to this general principle, several embodiments can be adapted.

According to an example, the cutting is made from the section of the migration exchange of a reel or from the bottom of the reel. According to another example, a web track is profiled on the calender by watering the web in the MD-direction at thick sections thereof. According to another third example, the tape strip/a paper strip is fed with a suitable feeding device in the MD-direction with the web to the reel, where the CD-profile of the reel is straightened by means of the said tape/paper strip. According to another fourth example, the desired bombering or pattern, which corrects the CD-profile, is made for example in the tampur stock on a tampur roll with a help of a MD-directional tape/paper strip. Then it can be advantageous that the tape fastening or the adaptation of the strip is made, advantageously, automatically, whereby a better CD-profile is obtained to the following machine reel according to CD-directional hardness profile that has been measured towards the end of the previous machine reel. According to another fifth example, the material web is covered at the sections of faults of the CD-profile that have been locally perceived in the MD-direction.

For the measuring of the CD-directional hardness profile of the goals of the invention in question and especially of the reel it is generally characteristic that the course of the measuring head loaded by the load tool is linear essentially to the invention in question.

This will be advantageous from the point of view of the measuring exactness when the material web reel increases in the radius direction.

According to a performance example of the invention that has been considered advantageous the linear motion course and load can be accomplished for example so that the load tool includes a power cylinder for example a compressed air cylinder or a hydraulic cylinder, a linear motor, a screw or a corresponding linear unit, which accomplishes a linear motion course. It is especially advantageous, in that case, that the linear course of the measuring head is parallel with the radius of the material web reel essentially. In that case, the measuring direction will be constant essentially and the measuring errors caused by the gravity which are typical of the known technique do not get to the birth.

According to an aspect of the invention it is advantageous that the measuring head is a measuring wheel, which in addition to the measuring and/or instead of the hardness profile measures the diameter profile and/or the surface velocity profile of the material web reel with a pulse transducer, whereby the diameter differences and surface velocity difference correlates directly with the thickness profile of the material web.

One can state about the advantages of the measuring device according to the invention, in the measuring of the generally linear hardness profile, that the motion course can be cost-effectively carried out as such with known components and that the space requirement of the measuring device is smaller than essentially known and that the linear load functions without problems and without danger for the materialising of measuring errors without the long and lever-like load stem, whereby an attempt has been made to minimize measuring errors earlier, the space requirement needed by the measuring arrangements which makes more reasonable investment possibilities possible.

About the advantages of the invention that can be especially mentioned the ones that have been eliminated or thanks to smaller measuring errors the accomplished measuring results can be adapted at least essentially according to the invention to the control of the reeling event of the material web and to the adjustment of the profiling devices of the material web, which precede reeling.

For other special characteristics of the invention the following special part of the explanation where an advantageous realization form of the invention has been explained when the material web machine is a paper machine is referred to by referring to enclosed ones, patent drawings.

BRIEF DESCRIPTION OF THE DRAWINGS

FIG. 2 illustrates an ultrasonic measuring as the measuring of the strain of layers, which are topmost of the surface layers of the reel.

FIG. 3 illustrates the measuring of the pulling, which causes strains inside the material web reel.

DESCRIPTION OF THE PREFERRED EMBODIMENTS

Figure 1:
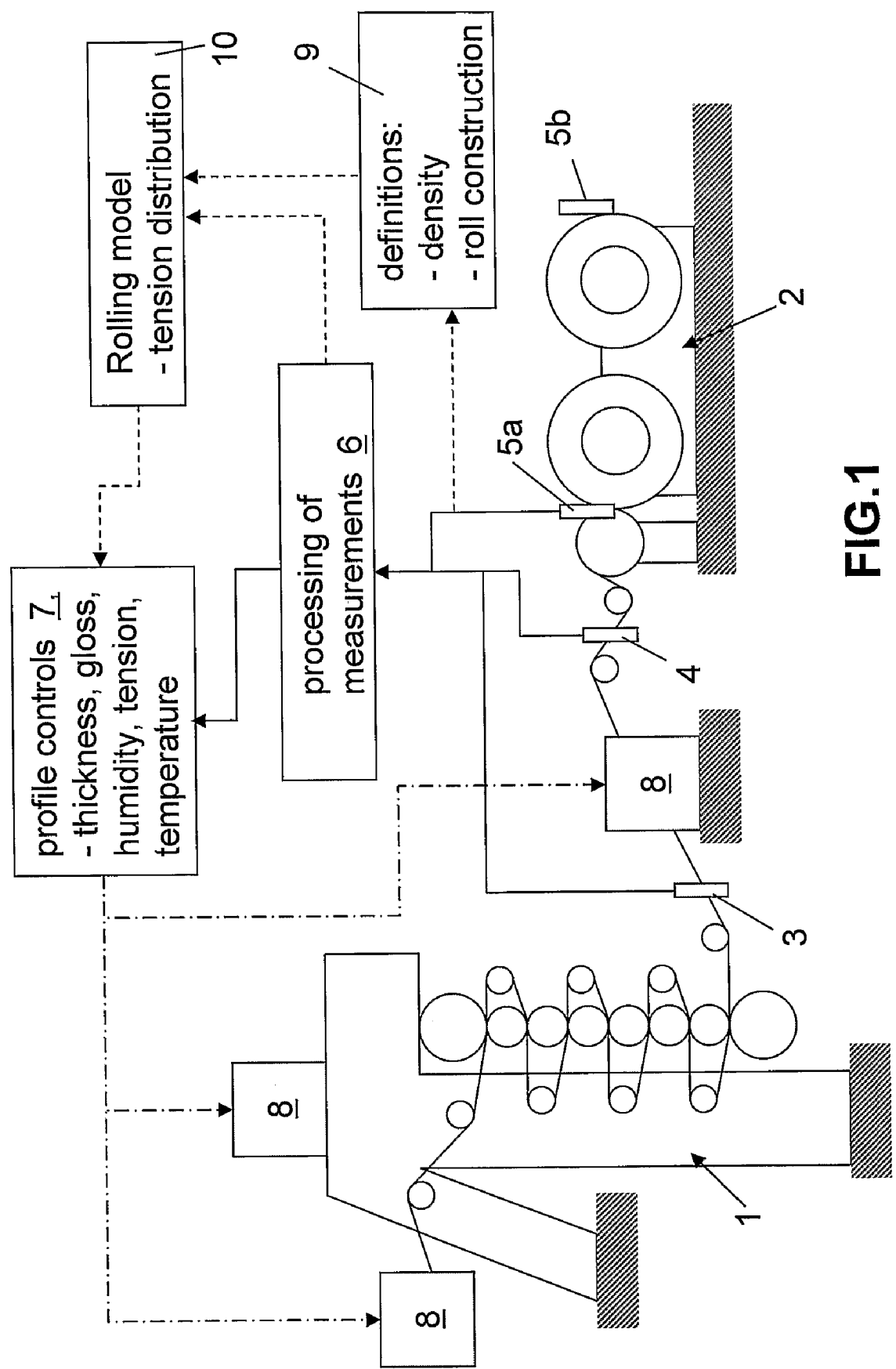
FIG. 1 diagrammatically represents the control of the reeling profile according to the invention arranged in the connection of a calender and reel-up to the dry end of the paper machine.

In the example of FIG. 1 profiling devices 8 which can be among others according to the invention:

feeding tools of the fiber suspension arranged in the head box by adjusting the feeding of which in the CD-direction the smoothness of the fiber suspension can be directed in the CD-direction with the help of heat and pressure the material web is profiled by compression cylinders in the CD-direction and/or reel-ups for example in a pressing unit and in a drying unit and in a calender 1, in the CD-direction, the profiling drying cylinders affect profilings of the material web with the help of the heat or reel-ups for example in drying unit and calender in the CD-direction the humidifiers, evaporators and vapor boxes of the material web affect profiling of the material web for example with the help of the heat in a drying unit and calender unit the adjusting devices of the track tightness of the material web track, which can be located in different places between the wet end of the material web machine and a dry head and which affect the MD-directional track tightness of the material web and in one CD-direction of the others to the material web affect profiling of the material web with the help of pressure and heat with affecting devices and the adjusting devices of the thickness of the material web etc. whereby the thickness of the material web track can be influenced in the wet end of the material web machine placed for example in a pressing unit and/or head box.

It is to be noted that so the placing of profiling devices is optional and according to the invention the profiling devices can be located except on the calender also before calender and/or after calender before reel-up 2 thus. There are three measuring stations in the performance example of FIG. 1 presented so that the first measuring station 3 will be after a calendar 1 and before the profiling devices that have been placed after the calendar, the second measuring station 4 is after the profiling devices that have been placed after the calendar 1 and before reel-up 2 and the third measuring station 4 and 5a, 5b are placed in the reel-up 2 in connection with reeling nips.

In the embodiment example of FIG. 1, the 4 measuring data is received to the processing unit 6 of the measurings from the first, second and third measuring station, in other words from two measuring stations 3, 4, which are located after the calendar 1 but before the reel-up 2 and from one measuring station 5a, 5b, which is related to a reeling nip of the reel-up. The measuring data that has been received from handling unit 6 of the measurings is moved as wired and/or wirelessly to adjustment unit 7 of the profile, from which the adjustment signals are transmitted to the profiling devices 8, which adjust the CD-profile of the web and which are located except on the calender also before calender and/or after calender before reel-up 2 according to the invention. According to the invention the profiling devices 8 can be for example profiling CD-reel-ups; humidifiers; dryers, vapor boxes; dryers; and track strain organs.

As it is shown in the performance form of FIG. 1 as the measuring data can be a model information of the reeling, which can be, for example, a division data of strain that is formed in a reeling model unit 10 basing on measuring data, which is received to hereto from a handling unit 6 and from definition data received thereto from a definition data unit 9, which model information is received by a profile adjustment unit 7, from the adjustment unit 7 of the profile, the control signals are transmitted to the profiling devices 8, which adjust the CD-profile of the web.

A comprehensive optimum control of the profiling devices 8 has been carried out so that, in the control, attention is paid both to qualitative (a web, for example paper technical) objectives set for the CD-profiles and objectives set for the CD-profiles of the reel 30. The simultaneous control of several CD-profiles can be carried out by many separate techniques for example by using optimisation methods, such as multi-objective optimizing combined the cost function, fine function or stress, or dynamic adjustment methods, MPC adjustment, LQ adjustment, state adjustment.

According to the invention the measurings to be obtained can be utilized from the third measuring stations 5a, 5b, which are located in the reel-up 2, when for example the reel cylinder of the reel-up, for example a polymer coated or a rubber coated reeling cylinder and/or a reeling core is censored by operating the stretch slip sensors and/or pressure sensors etc. sensors. The measurings of the reeling core can be utilized especially to a calibration and the measuring of the compression profile inside the material web reel to be formed. With measuring stations 4, which are located before the reel-up 2, the track tightness and possibly also temperature of the web are typically measured for managing thickness/(a density) of the web, i.e. for controlling profiles, so that the CD-profiles of the forming reel 30 is wanted. According to the invention, it is advantageous that the sensors have been placed in to give in the CD-direction a measuring, which reaches over the whole reel-up. The suitable measuring result will be reached for example with a spiral-like censoring. By means of the measurings by tension strips, for example, and by means of the data distribution of the compression to be received from the reeling model unit 10 one can determine both the support forces of the web during the bottom formation of the reel 30, whereby of hard reeling, there will be in the radius direction 10-20 cm of the material web, such as for example paper, at the beginning of the reeling on the reeling cylinder and the values of the modulus of elasticity of the web in direction of radius and tangent of the reel 30, the measuring signals can be transmitted from the reeling cylinder from the measuring station/stations 3, 4, 5a, 5b to control system 6, 7, whereby, for example, wireless telemetry can be utilised.

According to the invention advantageous that the measuring data to be obtained is used for the control of the center paragraph of the line load of the reeling flip, primarily of the track tightness of the web track, of reeling, especially during the bottom formations of the reel 30 from the third measuring station 5a, 5b, which is thus related to the reeling nip is. If necessary, the measuring data is also obtained to the control of the tightness and thickness (/a density) profiles, which take place in reel-up phase from the second measuring stations 4, which are located before the reel-up 2 to accomplish the bottom of the reel which is hard enough.

Such measuring data can be used from the first, second and third measuring station 3, 4, 5a, 5b, as the addition of the measuring data to be obtained, to manage on one hand the reeling nip in the reel-up 2 and on the other hand the web profile before the reel-up 2. According to the general basic idea of the invention, the measuring data to be obtained are processed in the handling unit 6 of the measurements, from which a unit the processed measuring data is transferred by wired means and/or wirelessly into an input line of the adjustment unit 7 of the profiles and the output-signals of the adjustment unit of the profile are utilized both for the reeling nip of the reel-up 2 (a line load, track tightness, center torque) and for managing, i.e. for controlling tightness and thickness(/a density) profiles of the web, which take place before the reel-up, such that the CD-profiles of the forming reel 30 is obtained wanted.

The measurings that are obtained from the reel-up 2, i.e. from the third measuring station 5a, 5b, can be used also for an adjustment of the quality of the web, which takes place with the calendar 1, that is, if, for example, the measurings, which are obtained from the quality indicators, for example the thickness profile, are not reliable. Then numerous known stochastic and statistics methods can be used for classification, comparison and the choice of measure signals.

The above mentioned reeling models can be so-called FEM models or the simplified reeling process model, such as the following model, which has been presented in a publication (T. Rand, L Ericsson; Physical Properties of Newsprint Reels during Winding. Peg 56 (1973): 6,153-156) And which describes effects between the separate reeling variables:

$$P_c = \frac{T}{d}\frac{1}{\alpha-1}\left(1-\left\{\frac{R}{R_2}\right\}^{\alpha-1}\right)$$

$$P_t = \frac{T}{d}\frac{1}{\alpha-1}\left(\alpha\left\{\frac{R}{R_2}\right\}^{\alpha-1}-1\right)$$

$\alpha = N_{ot}E_c$ in what $P_c$=parallel with the radius of the reel compression
$P_t$=parallel with the tangent of the reel compression
T=reeling tightness of the web
d=thickness of the paper
R=radius of the reel
$R_2$=outer radius of the reel
$N_{ot}$=modulus of elasticity in the direction of the tangent
$E_c$=modulus of elasticity in the direction of the radius.
Publication (H. Altman; Formulas for Computing Stresses in Center-Wound Reels. Basing to the Tappi 51 (1968): 4,176-179) one can state that there dominates, between the compressions with the tangent and radius compressions, a connection:

$P_c+P_t+d\,P_c/dr=0$ $r=R/R_\theta$ in what $R_\theta$=outer radius of the reeling reel-up.

The homogeneities, for example density, strain of the inner structure of the reel 30 and structure can be measured for example using the ultrasound. In the ultrasonic measuring, one can utilize in the paper track or on surface thereof opaque matter, which is as such known also from the medicine. Because the measuring (the measuring of the reflected echoes), which is based on the ultrasound, which is an unbroken material measuring method (Non Destructing Testing), the same can be used for the locating of internal density differences (hard/loose) in the reel (the direction of the radius/the CD-direction). By utilizing furthermore, the similar approach as to be adapted an ultrasonic measuring in the measuring of the thicknesses of the thin coating layers, one can measure by means of the method changes in the thickness of the paper on the reel. Such measuring data can be used as in addition of the measuring data to be obtained from the measuring stations 4, 5a, 5b both in the reel-up 2 to manage a reeling nip (a line load, track tightness, center torque) and before the reel-up 2 to manage, in other for managing strain/thickness/(density) profiles, which take place in webs, such that CD-profiles of the forming reel is as wanted.

According to an aspect of the invention, the goal is to make possible control of the reeling and the control of the internal tightness δ of the reel 30 in addition to the control of the reeling profile. This goal has been reached generally with a ultrasonic measuring. The ultrasound can be used to measure strains from inside the reel and/or from the surface layers. In that case, the measuring is based on the transition period of the ultrasound which will shorten when the strain increases.

Reference is made to FIG. 2, which illustrates the ultrasonic measuring from the surface layers of the reel for measuring by ultrasonic measuring strain of layers, which are the topmost surface layers of the paper reel. The progress time of the signal increases with the paper/the tightness increases. According to the embodiment example of FIG. 2, reeling parameters can be adjusted by the measuring data to be obtained. In the embodiment example of FIG. 2, the distances between the censor heads remain most advantageously continuously constant L, whereby the changes in the strain of the paper reel 20 can be fast perceived according to the invention.

Reference is made to FIG. 3, which illustrates the measuring of the pulling, which causes strains inside the paper reel. In the performance example of FIG. 3 the progress time of the ultrasonic signal is measured in the direction of the radius of the paper reel from two different sections. The distance of the ultrasonic sensor heads' 20 from each other is most advantageously continuously constant L. Then the pulling/tightness, which is directed to the paper reel, can be measured. When the strain difference and thus also the progression time difference of the signals between different measuring points are known, the paper reel's internal strains, especially at the surface area of the paper reel, can be determined and thus one can optimize the effect of reeling parameters to the paper reel for managing the profile of the forming paper reel.

There is further an object, according to an aspect of the present invention, a solution, which makes possible to examine of the quality of the formed paper reel, especially to examining of the quality of the machine reel before its transition to the unwinder. The quality of the machine reel can be examined on a scanning station, which is arranged in an intermediate storage of the machine reels or a corresponding, which is arranged between a reel-up and an in-line cutting station or a corresponding, where scanning station the reel's 30 structure is studied by scanning a comprehensive 3D model (3D, three dimensional) as possible from the reel.

In the scanning station the reel 30 is examined according to the invention by means of ultrasound, electromagnetic radiation or a corresponding signal, which penetrates inside the reel. It is possible to analyze from the received responses, the density variations, the tears of the reel, the reeling faults and the damages caused by handling and storage of the reel.

According to the invention it is the most advantageous that the quality of the machine reel is scanned just before the unwinding or possibly during reel-up, whereby the profiles of the forming reel 30 can be essentially directly influenced. It is advantageous to supplement the scanning by an expert system, by a neural network model and/or by the 3D model of the density, which concludes the type of the fault on the ends, the surface and/or inside of the reel.

In the unwinding of the cutting station or with a separate intermediate reel-up can be automatically removed from the reel those bad or damaged sections that have been found by scanning, when it is known where sections of the reel the faults are in. As examples about devices and methods, by which one can remove faults that have been perceived by scanning can be mentioned:
- an intermediate reel-up,
- automatic slabbing,
- slowing of the unwinder,
- automatic cutting of the web and feeding into a pulpier by means of the unwinder past a fault section, or
- Etc. equipment, by which the perceived fault is removed from the machine reel before it causes problems in the cutting or reject of customer reels.

The measuring of the qualities of the reel 30 during the unwinding is not always enough, because the speeds of the cutting stations are growing so big that one does not have time to slow down the machine, when the fault sections, which have been perceived in the unwinding, come against any more. Therefore the scanning, according to the invention, is likely to locate potential fault sections, whereby the speed of the cutting station can be automatically slowed down when approaching a scanned fault section. It is to be noted that a scanning station can be arranged except in the unwinder also in the reel-up.

It will be advantageous, when the additional information or definition information, which describes the handling process of the web, is used one way or another in addition to the measuring data, that the measuring data that has been concerned with will be directed from additional data unit or definition data unit 9 first into the reeling model unit 10, which forms for example a strain distribution data of the information the additional information in question or definition information and transmits in a wired manner or wirelessly the strain distribution data together with the processed measure data to an input channel of the adjustment unit 7 of the profile. The output signals of the adjustment unit 7 of the profile are used to manage, i.e. to control:
- profiling devices 8, which are locating optionally before the calender 1, in the calender or after the calender,
- track tightness profiles and thickness(/a density) profiles of the web, which take place before the reel-up 2,
- line load, center torque of the reeling nip, so that the reel's to be formed 30 CD—the profiles are obtained wanted.

According to an embodiment of the invention, which has been considered especially advantageous, to CD-profile the material web reel 30, especially to straighten the CD-profile, a narrow strip is cut from the web in the MD-direction from the point of the thick web or in the reel-up 2 directly from the surface of the reel. According to this general principle, several adaptations can be applied.

To CD-profile actively the material web reel 30 especially to straighten CD-profile it could be one possibility to cut at a change section of the reel 30 the reel or the web W from the bottom of the reel,
- it is a second possibility is that the web is profiled already on the calender 1 by watering a thick section of the web in MD-direction,
- it is a third possibility is that with a suitable feeding device a tape/paper strip is fed in MD-direction with the web to the reel, whereby the tape/paper strip tries to straighten the CD-profile of the reel,
- it is the fourth possibility that a desired bombering or pattern, which corrects the CD-profile, is made for example by means of a tampur roller for example in a tampur stock, it is advantageous that a taping or adapting a paper strip is made most advantageously automatically at the output side of the preceding machine in accordance with the measured CD-directional hardness profile, whereby a better CD-profile is obtained to the following machine reel, and
- the fifth possibility is that the material web is covered locally in the MD-direction at faults of the CD-profile sections that have been perceived.

Figure 4:
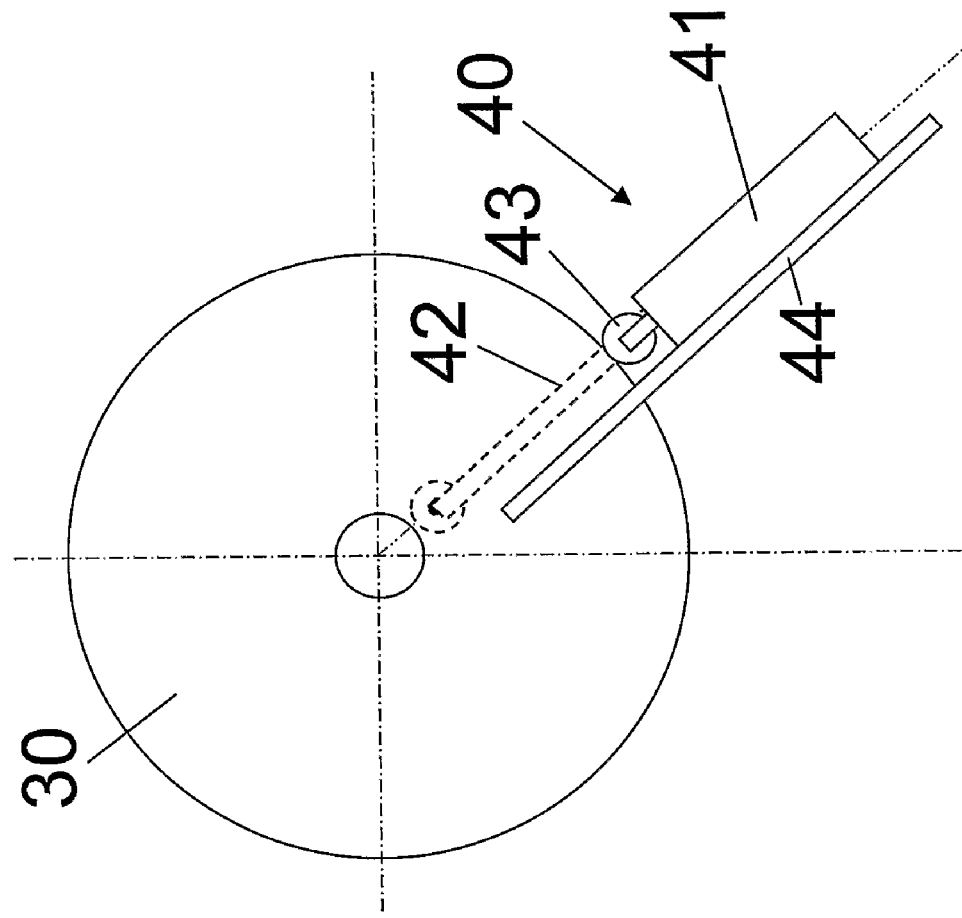
FIG. 4 represents as the measuring of the CD-directional hardness profile of the material web reel the measuring device which is in accordance with the invention diagrammatically out.

Reference is made to FIG. 4, which presents schematically a measuring device 40 according to the invention, for measuring a CD-directional hardness profile of the material web reel.

In the embodiment example according to FIG. 4, the measuring device 40 includes for the measuring of the CD-directional hardness profiles of material web reel 30 a measuring head 43, which is loaded by a loading means 41, 42 against the outer surface of the material web reel, which rotates around its central axis of rotations and which when turning grows in the direction of the radius. According to the invention, the loading means loads the measuring head, so that the motion course will be a linear motion course continuously, when the material web reel while turning grows in the radius direction. In that case, the measuring direction will be constant essentially and the measuring errors caused by the gravity, which are typical of the prior art, do not get to be formed.

To accomplish the linear motion course the loading means 41, 42 of the measuring device 40 can be for example a power cylinder, which has been presented in the figure, which power cylinder is a compressed air cylinder or hydraulic cylinder advantageously. Instead of the power cylinder, one can also apply other linear units, which accomplishes a linear motion course. This kind of a linear unit can be for example a linear motor or a screw tool.

According to the invention it is preferred that the linear motion of the measuring head 43 towards the outer surface of the material web reel 30 is essentially parallel with the radius of the material web reel. In that case, the measuring direction will be essentially constant and the measuring errors caused by the gravity which are typical of the prior art do not get to exist.

Figure 5A:
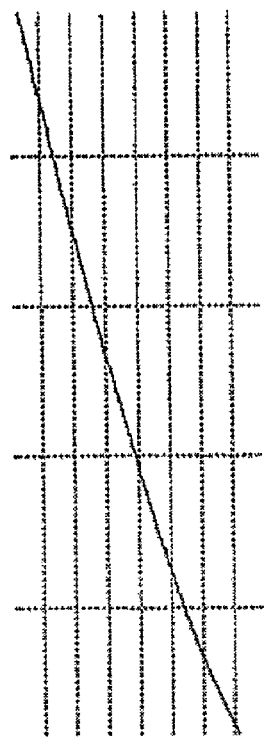
FIG. 5a will represent as a time function a result of a harness profile to be accomplished by the prior art measuring, when the driving speed of the reel is constant about 1000 m/min and when diameter of the reel.
Figure 5B:
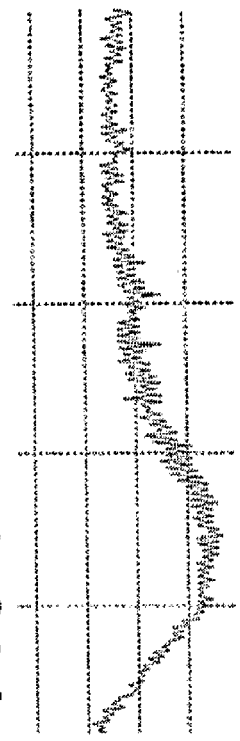
FIG. 5b will represent as a time function growth of the diameter of the reel by the measuring according to the present invention when the driving speed of the reel is constant about 1000 m/min.

Reference is made to FIG. 5a and to FIG. 5b. When the driving speed of the reel is constant about 1000 m/min, FIG. 5a represents a hardness profile as a function of time by means of measuring that in accordance with the prior art, and FIG. 5b represent the diameter of the reel growth as a function of time by means of measuring that in accordance with the prior art. One can notice that the loading bar, which moves in a pivoting manner and which moves and loads the measuring head along a curved track, causes due to a changing measuring geometry and gravity of the earth continues measuring error, which is appearing continues oscillation of the function that describes the CD-directional hardness profile. By means of the measuring device according to the invention, one can eliminate this kind of a curved motion course of the measuring head, and whereas the motion course is continuously linear the gravity of the earth does either not cause measuring error. In that case the function, which describes a CD-directional hardness profile, will remain steady better and describes more sensitively and in more detail the CD-directional hardness profiles of the material web reel 30, which make possible to detect possible web faults faster.

It is further stated, that concerning the measuring device according to the invention, that the measuring head 43, which is for example a measuring wheel, can be used to measure the diameter profiles and/or the surface velocity profile of the material web reel 30, in addition to and/or instead of the measuring of the hardness profile, by adapting a pulse transducer furthermore therewith. In that case, the diameter differences and surface velocity difference to be perceived and/or measured will correlate directly with the thickness profile W of the material web W.

The present invention has been described above only means of a method and an arrangement which are related to a calender. Naturally, the present invention has not been meant to be limited to relate this kind of an individual embodiment or field of application in any way but many equivalent and alternative solutions and modifications are possible within the scope of the inventive idea that has been defined in the enclosed patent claims.

In addition to the above mentioned head box, the pressing unit, the drying unit, the calender unit, the basic idea of the invention can be applied also for example in connection with the covering station to manage the CD-directional profile for making an improved reeling possible.

In the presented method also all the known measuring methods or the variations of methods, which are suitable for a profile measuring, such as a traversing measure head or a row sensor techniques, can be used for the determination of the hardness and structure of the reel 30.

The invention claimed is:

1. A method of controlling a reeling profile of a fiber web in a paper or cardboard machine, the direction of travel defining a machine direction, and a cross machine direction, the fiber web having a cross machine direction profile, the method comprising the steps of:
    selecting a qualitative objective for the cross machine direction profile of the fiber web related to paper type;
    selecting an objective for cross machine direction reeling profiles of a reel to be formed;
    forming a fiber web;
    passing the fiber web through a calendar;
    forming the fiber web into a fiber web reel in a reel-up, the reel forming a reeling nip with a winding drum;
    measuring a first cross machine direction profile of the web at a first position upstream in the machine direction from the reel-up to form a measured cross machine direction profile of the web;
    measuring a line load cross machine direction profile of the reeling nip to form a measured line load cross machine direction profile of the reeling nip; and
    before the first position, adjusting the cross machine direction profile of the fiber web based on the measured line load cross machine direction profile of the reeling nip, and the first cross machine direction profile; and
    wherein the cross machine direction profile of the fiber web is controlled to simultaneously optimize the cross machine direction profile in accordance with the selected qualitative objective of the web, and the selected objective for the cross machine direction reeling profiles of a reel.

2. The method of claim 1 wherein the step of adjusting the cross machine direction profile of the fiber web is performed in a headbox which is used to form the fiber web.

3. The method of claim 1 wherein the step of adjusting the cross machine direction profile of the fiber web is performed by controlling heat or pressure in a pressing unit which is used to de-water the web before the calendar.

4. The method of claim 1 wherein the step of adjusting the cross machine direction profile of the fiber web is performed by controlling cross machine direction heat, pressure, or humidity in the calendar.

5. The method of claim 4 wherein the step of forming the fiber web into a fiber web reel in a reel-up further comprises:
    obtaining measuring data before the step of adjusting the cross machine direction profile of the fiber web, at a first measuring station;
    obtaining measuring data after the step of adjusting the cross machine direction profile of the fiber web, at a second measuring station; and
    measuring the line load cross machine direction profile of the reeling nip at a third measuring station to obtain measuring data; and
    managing the step of adjusting the cross machine direction profile of the fiber web with measuring data obtained from the first, second, and third measuring stations.

6. The method of claim 5 wherein the measuring data obtained from the first measuring station and the second measuring station consists of data selected from the group consisting of thickness, luster, moisture, grammage, density, roughness, track tightness of the fiber and permeability.

7. The method of claim 1 wherein the selected qualitative objective for a cross machine direction profile of the web related to paper type is thickness.

8. The method of claim 1 wherein the objective for the cross machine direction reeling profiles of the reel to be formed is compression profiles inside the material web reel to be formed.

9. The method of claim 1 wherein the control to simultaneously optimize the cross machine direction profile in accordance with the selected qualitative objective, and the selected objective for the cross machine direction reeling profiles of the reel, is according to dynamic adjustment, MPC adjustment, or LQ adjustment methods.

10. A method of controlling a reeling profile of a fiber web in a paper or cardboard machine, the direction of travel defining a machine direction, and a cross machine direction, the fiber web having a cross machine direction thickness profile, the method comprising the steps of:
  selecting a qualitative objective for the cross machine direction thickness profile of the web related to paper type;
  selecting an objective for cross machine direction reeling profiles of a reel to be formed;
  forming a fiber web;
  passing the fiber web through a calendar;
  reeling the fiber web to form a fiber web reel in a reel-up, the reel forming a reeling nip with a winding drum;
  measuring a first cross machine direction thickness profile of the web at a first position upstream in the machine direction from the reel-up to form a measured cross machine direction profile of the web;
  measuring a cross machine direction hardness or diameter profile of the forming fiber web reel to from a measured cross machine direction hardness or diameter profile of the reel;
  before the reel-up, adjusting the cross machine direction thickness profile of the fiber web based on the measured cross machine direction hardness or diameter profile of the forming fiber web reel; and
  wherein the cross machine direction thickness profile of the fiber web is controlled to simultaneously optimize the cross machine direction thickness profile of the fiber web in accordance with the selected qualitative objective of the cross machine direction thickness profile of the fiber web and the selected objective for the cross machine direction reeling profiles of the reel.

11. The method of claim 10 wherein the step of adjusting the cross machine direction thickness profile of the fiber web is performed in a headbox which is used to form the fiber web.

12. The method of claim 10 wherein the step of adjusting the cross machine direction thickness profile of the fiber web is performed by controlling heat or pressure in a pressing unit which is used to de-water the web before the calendar.

13. The method of claim 10 wherein the step of adjusting the cross machine direction thickness profile of the fiber web is performed by controlling cross machine direction heat, pressure, or humidity in the calendar.

14. The method of claim 13 wherein the step of reeling the fiber web to form a fiber web reel in a reel-up further comprises:
  obtaining measuring data before the step of adjusting the cross machine direction thickness profile of the fiber web, at a first measuring station;
  obtaining measuring data after the step of adjusting the cross machine direction thickness profile of the fiber web, at a second measuring station; and
  measuring the line load cross machine direction profile of the reeling nip at a third measuring station to obtain measuring data; and
  managing the step of adjusting the cross machine direction thickness profile of the fiber web with measuring data obtained from the first, second, and third measuring stations.

15. The method of claim 14 wherein the measuring data obtained from the first measuring station and the second measuring station consists of data selected from the group consisting of thickness, luster, moisture, grammage, density, roughness, track tightness of the fiber and permeability.

16. A method of controlling a reeling profile of a fiber web in a paper or cardboard machine, the direction of travel defining a machine direction, and a cross machine direction, the fiber web having a cross machine direction profile, the method comprising the steps of:
  selecting a cross machine direction profile of the web related to paper type;
  selecting internal strain cross machine direction reeling profiles of a reel to be formed;
  forming a fiber web;
  passing the fiber web through a calendar;
  forming the fiber web into a fiber web reel in a reel-up, the reel forming a reeling nip with a winding drum;
  measuring a first cross machine direction profile of the web at a first position upstream in the machine direction from the reel-up to form a measured cross machine direction profile of the web;
  measuring an internal strain cross machine direction profile of the reel wherein the reel has surface layers, by ultrasonic measuring from the surface layers of the reel the internal strains of the surface layers; and
  before the first position, adjusting the cross machine direction profile of the fiber web based on the measured internal strain cross machine direction profile of the reel, and the first cross machine direction profile of the fiber web; and
  wherein the cross machine direction profile of the fiber web is controlled to simultaneously optimize the cross machine direction profile of the fiber web to the selected cross machine direction profile of the web related to paper type, and the selected internal strain cross machine direction reel profiles.

* * * * *

UNITED STATES PATENT AND TRADEMARK OFFICE
CERTIFICATE OF CORRECTION

| | |
|---|---|
| PATENT NO. | : 7,799,171 B2 |
| APPLICATION NO. | : 11/571207 |
| DATED | : September 21, 2010 |
| INVENTOR(S) | : Mäenpää et al. |

Page 1 of 1

It is certified that error appears in the above-identified patent and that said Letters Patent is hereby corrected as shown below:

On the first page of the issued patent, the title "REELING METHOD AND SYSTEM AS WELL AS AN MEASURING APPARATUS" should be -- REELING METHOD AND SYSTEM AS WELL AS A MEASURING APPARATUS --.

On the first page of the issued patent, the PCT Pub. Date: "Dec. 1, 2006" should be -- Jan. 12, 2006 --.

Column 9, line 35, "load of the reeling flip" should be -- load of the reeling nip --.

Column 12, line 43, "that a desired bombering" should be -- that a desired bombeering --.

Column 14, line 13, "through a calendar" should be -- through a calender --.

Column 14, line 40, "before the calendar" should be -- before the calender --.

Column 14, line 44, "humidity in the calendar" should be -- humidity in the calender --.

Column 15, line 22, "through a calendar" should be -- through a calender --.

Column 15, line 50, "before the calendar" should be -- before the calender --.

Column 15, line 54, "humidity in the calendar" should be -- humidity in the calender --.

Column 16, line 32, "through a calendar" should be -- through a calender --.

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,799,171 B2  
APPLICATION NO. : 11/571207  
DATED : September 21, 2010  
INVENTOR(S) : Mäenpää et al.

Page 1 of 1

It is certified that error appears in the above-identified patent and that said Letters Patent is hereby corrected as shown below:

Title Page, Item (54) and at Column 1, lines 1 and 2, the title "REELING METHOD AND SYSTEM AS WELL AS AN MEASURING APPARATUS" should be -- REELING METHOD AND SYSTEM AS WELL AS A MEASURING APPARATUS --.

On the first page of the issued patent, the PCT Pub. Date: "Dec. 1, 2006" should be -- Jan. 12, 2006 --.

Column 9, line 35, "load of the reeling flip" should be -- load of the reeling nip --.

Column 12, line 43, "that a desired bombering" should be -- that a desired bombeering --.

Column 14, line 13, "through a calendar" should be -- through a calender --.

Column 14, line 40, "before the calendar" should be -- before the calender --.

Column 14, line 44, "humidity in the calendar" should be -- humidity in the calender --.

Column 15, line 22, "through a calendar" should be -- through a calender --.

Column 15, line 50, "before the calendar" should be -- before the calender --.

Column 15, line 54, "humidity in the calendar" should be -- humidity in the calender --.

Column 16, line 32, "through a calendar" should be -- through a calender --.

This certificate supersedes the Certificate of Correction issued August 9, 2011.

Signed and Sealed this  
Thirtieth Day of August, 2011

David J. Kappos  
*Director of the United States Patent and Trademark Office*